(12) United States Patent
Eberman et al.

(10) Patent No.: US 12,368,311 B2
(45) Date of Patent: Jul. 22, 2025

(54) SYSTEM AND METHOD FOR ELECTRONIC DEVICE

(71) Applicant: 3M INNOVATIVE PROPERTIES COMPANY, St. Paul, MN (US)

(72) Inventors: Kevin W. Eberman, St. Paul, MN (US); Jason A. Graves, Darlington (GB)

(73) Assignee: 3M Innovative Properties Company, St. Paul, MN (US)

( * ) Notice: Subject to any disclaimer, the term of this patent is extended or adjusted under 35 U.S.C. 154(b) by 681 days.

(21) Appl. No.: 17/754,438

(22) PCT Filed: Sep. 24, 2020

(86) PCT No.: PCT/IB2020/058924
§ 371 (c)(1),
(2) Date: Apr. 1, 2022

(87) PCT Pub. No.: WO2021/064523
PCT Pub. Date: Apr. 8, 2021

(65) Prior Publication Data
US 2022/0407325 A1  Dec. 22, 2022

Related U.S. Application Data

(60) Provisional application No. 62/910,148, filed on Oct. 3, 2019.

(51) Int. Cl.
*H02J 7/00* (2006.01)
*A61F 11/14* (2006.01)
(Continued)

(52) U.S. Cl.
CPC .......... *H02J 7/0048* (2020.01); *A61F 11/145* (2022.01); *A62B 9/006* (2013.01);
(Continued)

(58) Field of Classification Search
CPC .. H02J 7/0048; H02J 7/00712; H02J 2310/54; H02J 7/0063; A61F 11/145;
(Continued)

(56) References Cited

U.S. PATENT DOCUMENTS 3,568,175 A     3/1971  Schwehr
3,932,797 A  *  1/1976  York ........................ H02H 7/18
                                                        340/661

(Continued)

FOREIGN PATENT DOCUMENTS

FR        3008621        1/2015

OTHER PUBLICATIONS

AUX_Bluetooth_Adapter_2022 11 pages Amazon.com:_AUX_Bluetooth_Adapter_for_Car_Music_Streaming,_Handsfree_Calls,_Portable_Bluetooth_Receiver_for_HomeStereo/Headphones.

(Continued)

*Primary Examiner* — Richard Isla
*Assistant Examiner* — John Ondrasik

(57) ABSTRACT

There is provided a system having an electronic device powered by at least one battery, a controller communicably coupled to at least one battery, wherein the controller is configured to: determine a state of charge of the at least one battery; and interrupt a function of the electronic device for at least one predefined time period based on the state of charge of the at least one battery, where the interruption is indicative of a state of charge of the at least one battery. There is also provided an electronic device for use in the system.

15 Claims, 4 Drawing Sheets

(51) Int. Cl.
*A62B 7/10* (2006.01)
*A62B 9/00* (2006.01)
*A62B 18/00* (2006.01)
*G10K 11/178* (2006.01)

(52) U.S. Cl.
CPC .......... *A62B 18/006* (2013.01); *G10K 11/178* (2013.01); *H02J 7/00712* (2020.01); *A62B 7/10* (2013.01); *G10K 2210/1081* (2013.01); *H02J 2310/54* (2020.01)

(58) Field of Classification Search
CPC ......... A62B 9/006; A62B 18/006; A62B 7/10; G10K 11/178; G10K 2210/1081
USPC ....................................................... 320/149, 3
See application file for complete search history.

(56) References Cited

U.S. PATENT DOCUMENTS

| | | |
|---|---|---|
| 7,059,338 B1 | 6/2006 | Kincaid et al. |
| 7,649,337 B2 | 1/2010 | Uehlein-Proctor et al. |
| 7,817,053 B2 | 10/2010 | Kusakari et al. |
| 2007/0240719 A1* | 10/2007 | Duarte ................. A62B 18/006 128/205.27 |
| 2008/0057857 A1* | 3/2008 | Smith .................. H04R 1/1033 455/3.05 |
| 2008/0304362 A1* | 12/2008 | Fleming ................. H04B 13/02 367/134 |
| 2009/0079398 A1* | 3/2009 | Saar ....................... H05B 45/40 315/200 A |
| 2012/0211563 A1 | 8/2012 | Gannon et al. |
| 2016/0070333 A1 | 3/2016 | Haruki et al. |

OTHER PUBLICATIONS

Universal Bluetooth Transmitter Car Kit information page from Amazon.com retrieved from the internet on Oct. 8, 2019, < http://www.amazon.com/Universal-Bluetooth-Transmitter-Handsfree-Microphone/dp/B0168CUAYO/ref=asc_df_B0168CUAYO/?tag=hyprod-20&linkCode=df0&hvadid=312026001792&hypos=1o2&hynetw=g&hyrand=18212052505332544271&hypone=&hyptwo=&hygmt=&hydey=c&hvdvcmdl=&hvlocint=&hvlocphy=9052389&hytargid=pla-570982704238&psc=1>, 1 page.

International Search Report for PCT Application No. PCT/IB20/58924 mailed on Apr. 2, 2021, 3 pages.

* cited by examiner

SYSTEM AND METHOD FOR ELECTRONIC DEVICE

CROSS REFERENCE TO RELATED APPLICATIONS

This application is a national stage filing under 35 U.S.C. 371 of PCT/IB2020/058924, filed Sep. 24, 2020, which claims the benefit of U.S. Provisional Application No. 62/910,148, filed Oct. 3, 2019, the disclosure of which is incorporated by reference in its/their entirety herein.

TECHNICAL FIELD

The present disclosure relates generally to a system and a method for an electronic device. In particular, the present disclosure relates to a charge indication system for an electronic device and a method therefore.

BACKGROUND

Generally, an electronic device powered by one or more batteries may include a charge indicator in order to indicate to a user a charge level in the electronic device. The charge indicator may be a Light Emitting Diode (LED) indicator, an audible indicator, a vibration indicator, and so on. However, in many situations, such charge indicators may be inaccessible to the user, in turn, limiting functionality and usability of the charge indicator. For example, in very brightly lit environments or when the electronic device is placed away from a direct view of the user, the user may be unable to distinguish or easily view the LED indicator. In another situation, such as in noisy environments, the user may be unable to hear the audible indicator. In yet another situation, such as during continuous movement of the user, the user may be unable to feel a buzz or vibration provided by the vibration indicator. Additionally, such charge indicators may be powered by the one or more batteries of the electronic device. As such, the charge indicator may drain useful charge of the battery, especially during low charge, and in turn, reduce a remaining runtime of the electronic device. Also, the charge indicator may add considerable bulk, complexity, and cost to the electronic device. Hence, there is a need for an improved charge indication system for such electronic devices.

SUMMARY

In one aspect, the present disclosure provides a system having an electronic device powered by at least one battery, a controller communicably coupled to at least one battery, where the controller is configured to: determine a state of charge of the at least one battery; and interrupt a function of the electronic device for at least one predefined time period based on the state of charge of the at least one battery, where the interruption is indicative of a state of charge of the at least one battery. In some embodiments, the system is a charge indication system for the electronic device. In some embodiments, the state of charge of the at least one battery is a low state of charge.

In some embodiments, the at least one predefined time period is implemented in an off-on pattern such that the electronic device is powered off for some time period and then powered on for a second time period. In some embodiments, a set of one or more interruptions do not substantially diminish intended function of the electronic device.

In some embodiments, the interruptions are configured to indicate a set of predefined states of charge. In some embodiments, the interruptions comprise approximately 1 milliseconds (ms), 10 ms, 100 ms, or 1 seconds (s) time periods that are separated from each other by time periods of approximately 1 ms, 10 ms, 100 ms, 1 s, or 10 s. In some embodiments, the interruptions comprise approximately 1 ms, 10 ms, 100 ms, time periods that are separated from each other by time periods of approximately 1 ms, 10 ms, 100 ms, or 1 s. In some embodiments, the interruptions comprise approximately 1 ms or 10 ms time periods that are separated from each other by time periods of approximately 1 ms, 10 ms, or 100 ms.

In another aspect, a charge indication system for an electronic device powered by at least one battery is provided. The charge indication system includes a controller communicably coupled to the at least one battery. The controller is configured to determine a state of charge of the at least one battery. The controller is also configured to interrupt a function of the electronic device for a predefined time period based on the state of charge of the at least one battery. Interrupting the function of the electronic device is indicative of a low state of charge of the at least one battery. As such, the charge indication system may provide a brief interruption of the function of the electronic device to indicate the state of charge of the at least one battery to an user without substantially disrupting a normal operation of the electronic device and without consuming valuable charge of the at least one battery during the low state of charge of the at least one battery.

In another aspect, an electronic device is provided. The electronic device includes at least one battery. The at least one battery includes one or more electrochemical cells. The electronic device also includes at least one component electrically connected to and powered by the at least one battery. The electronic device further includes a controller communicably coupled to the at least one battery and the at least one component. The controller is configured to determine a state of charge of the at least one battery. The controller is also configured to interrupt a function of the at least one component for a predefined time period based on the state of charge of the at least one battery. Interrupting the function of the at least one component is indicative of a low state of charge of the at least one battery. As such, the controller may indicate the state of charge of the at least one battery to the user without using additional visual, audible, and/or vibration indicators, in turn, reducing bulk, complexity, and cost of the electronic device.

In yet another aspect, a method of indicating charge level in an electronic device is provided. The electronic device includes at least one component powered by at least one battery. The method includes determining a state of charge of the at least one battery. The method also includes interrupting a function of the at least one component for a predefined time period based on the state of charge of the at least one battery. Interrupting the function of the at least one component is indicative of a low state of charge of the at least one battery.

BRIEF DESCRIPTION OF THE DRAWINGS

Exemplary embodiments disclosed herein may be more completely understood in consideration of the following detailed description in connection with the following figures. The figures are not necessarily drawn to scale. Like numbers used in the figures refer to like components. However, it will be understood that the use of a number to refer to a component in a given figure is not intended to limit the component in another figure labeled with the same number.

FIG. 1 is a perspective view of an exemplary electronic device, according to an embodiment of the present disclosure.

DETAILED DESCRIPTION

In the following description, reference is made to the accompanying figures that form a part thereof and in which various embodiments are shown by way of illustration. It is to be understood that other embodiments are contemplated and may be made without departing from the scope or spirit of the present disclosure. The following detailed description, therefore, is not to be taken in a limiting sense.

Figure 1:
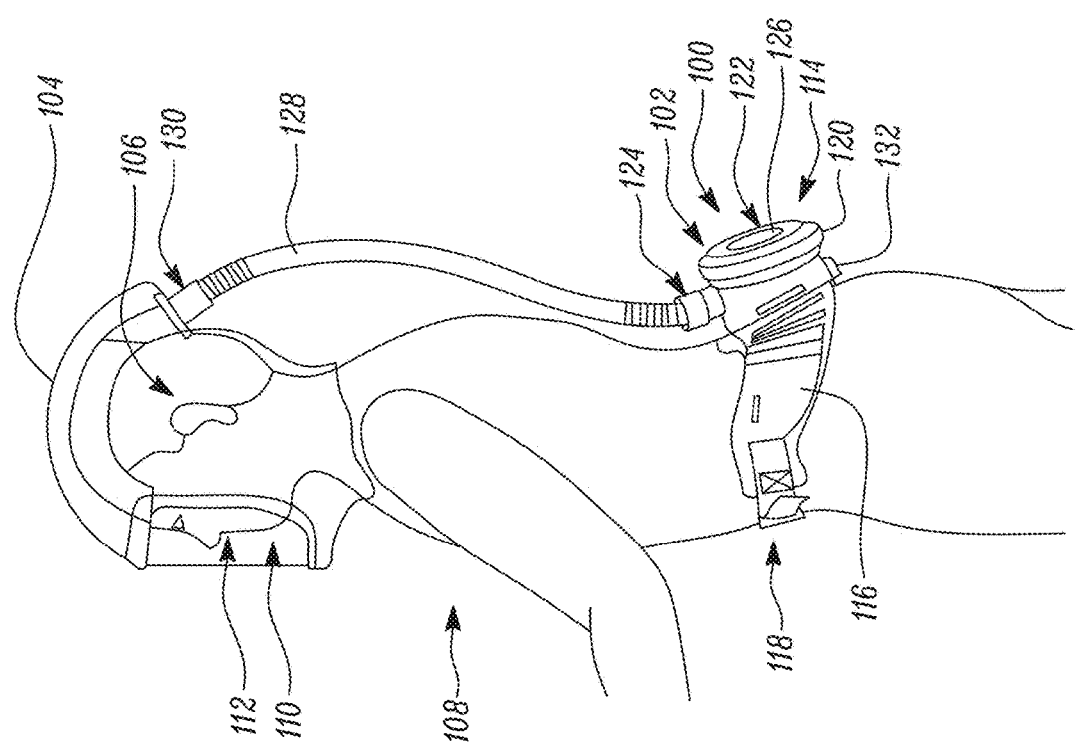

Referring to FIG. 1, a perspective view of an exemplary electronic device 100 is illustrated. The electronic device 100 will be hereinafter interchangeably referred to as the "device 100". In the illustrated embodiment, the electronic device 100 is a Powered Air Purifying Respirator (PAPR) 102. PAPR 102 will be hereinafter interchangeably referred to as the "respirator 102". Respirator 102 includes a headpiece 104. Headpiece 104 is adapted to be worn on a head portion 106 of a user 108. As such, headpiece 104 is adapted to at least partially enclose head portion 106 of user 108 to form a breathing zone 110. Breathing zone 110 is disposed substantially around a face portion 112 of user 108 to direct air toward nose and mouth of user 108. In the illustrated embodiment, headpiece 104 is a hood type headpiece. In some embodiments, headpiece 104 may be any other type of headpiece, such as a mask type headpiece, a helmet type headpiece, a body suit type headpiece, a full-face type headpiece, a half face type headpiece, and so on.

Respirator 102 also includes a blower 114. In some embodiments, blower 114 is attached to a belt 116. As such, blower 114 is adapted to be secured to a torso portion 118 of user 108 via belt 116. In some embodiments, blower 114 may be secured on user 108 using any other supporting arrangement, such as a backpack, a shoulder strap, and so on, based on application requirements. In some embodiments, blower 114 may be mounted directly on headpiece 104 of respirator 102, based on application requirements. Blower 114 includes a housing 120. Housing 120 defines an inlet 122 and an outlet 124 of blower 114. Inlet 122 is adapted to receive the air within blower 114 and outlet 124 is adapted to allow the air to exit from blower 114. Respirator 102 also includes a filter 126 disposed in inlet 122. Filter 126 is adapted to filter out particles, gases and/or vapors from the air entering blower 114 through inlet 122. Filter 126 may include a single or multiple filter unit(s), based on application requirements. Also, filter 126 may be disposed within blower 114 or outside of blower 114, based on application requirements.

Respirator 102 also includes a breathing tube 128 connected between outlet 124 of blower 114 and an inlet 130 of headpiece 104. Breathing tube 128 is adapted to supply air from blower 114 to headpiece 104. Respirator 102 includes at least one battery 132. In some embodiments, respirator 102 may include a single battery 132. In some embodiments, respirator 102 may include multiple batteries 132, such as a battery pack. Battery 132 is adapted to provided power supply to respirator 102 for operational requirements. In some embodiments, at least one battery 132 is mounted to blower 114. In other embodiments, at least one battery 132 may be mounted to belt 116 and away from blower 114 and connected to blower 114 using suitable wires/cables. In some embodiments, at least one battery 132 may be remote from respirator 102 and connected to blower 114 using suitable wires/cables.

Figure 2:
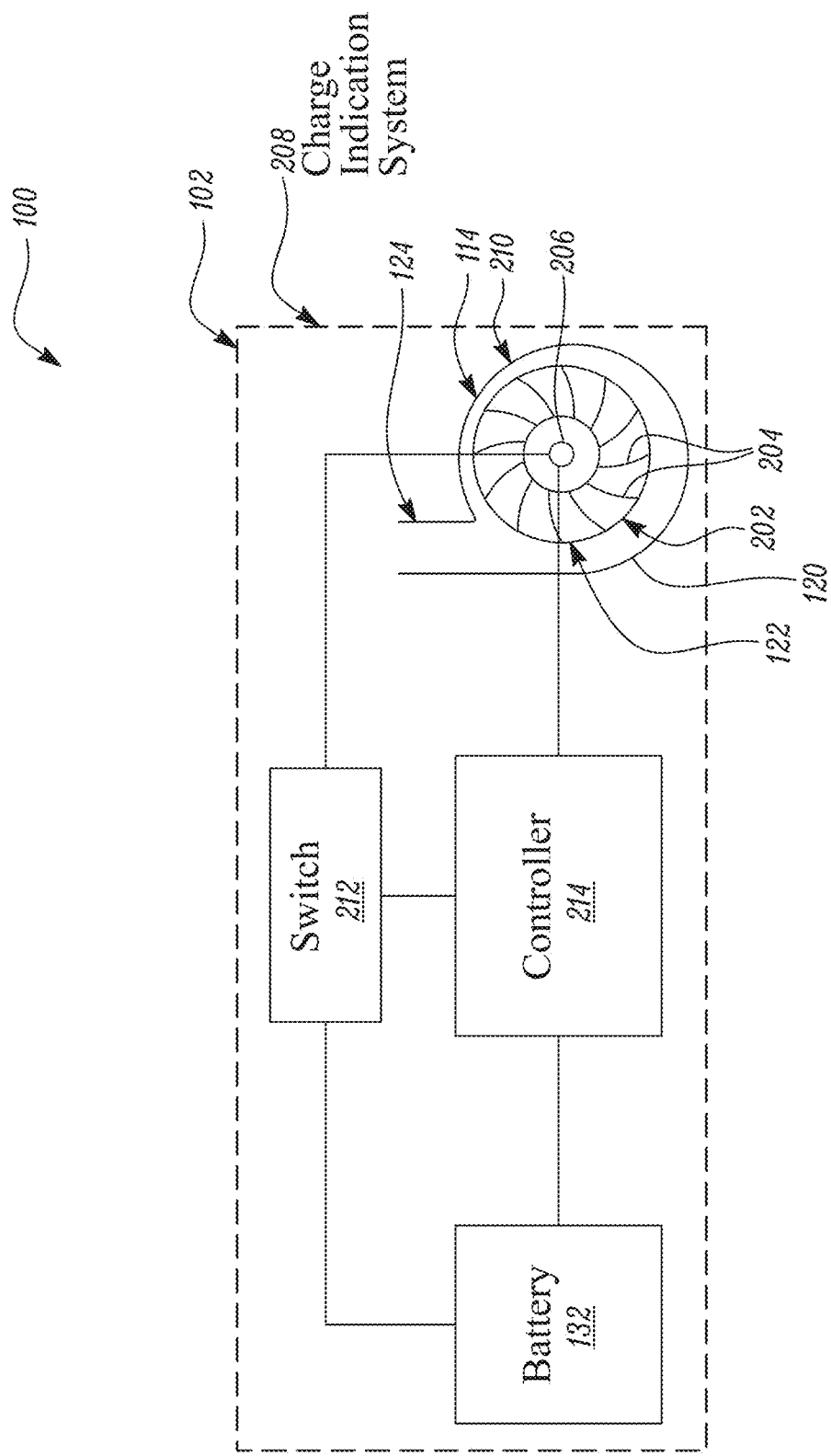
FIG. 2 is a schematic representation of a charge indication system for the electronic device of FIG. 1.

Referring to FIG. 2, a side view of exemplary blower 114 is illustrated. Blower 114 includes a fan 202 having a plurality of blades 204 disposed rotatably within housing 120. Fan 202 is operably coupled to a motor 206 adapted to rotatably drive fan 202. Accordingly, based on rotation of fan 202 by motor 206, blades 204 are adapted to draw air within blower 114 through inlet 122 and discharge air from blower 114 through outlet 124. In some embodiments, blower 114 is a centrifugal or radial type blower. In some embodiments, blower 114 may be any other type of blower, such as an axial type blower, and so on, based on application requirements. Also, motor 206 may be any electric or electronic motor, such as a direct current type motor, an alternating current type motor, a brushless type motor, a brush type motor, and so on, based on application requirements.

It should be noted that although device 100 is illustrated and described herein as PAPR 102 or respirator 102. In some embodiments, device 100 may be any other electronic device, such as an active noise cancellation headset (not shown). The active noise cancellation headset will be hereinafter interchangeably referred to as the "headset". In such a situation, the headset may include a driver (not shown) connected to a battery (not shown) of the headset. As such, the driver may receive power supply from the battery for operational requirements. The driver may be adapted to provide active noise cancellation function of the headset based on an activation of the driver.

FIG. 2 also illustrates a schematic representation of a system, such as a charge indication system, 208 for device 100. Charge indication system 208 will be hereinafter interchangeably referred to as the "system 208". In some embodiments, the system 208 has an electronic device 100 powered by at least one battery 132, a controller 214 communicably coupled to at least one battery 132, where the controller 214 is configured to: determine a state of charge of the at least one battery 132; and interrupt a function of the electronic device 100 for at least one predefined time period based on the state of charge of the at least one battery 132, where the interruption is indicative of a state of charge of the at least one battery 132. In some embodiments, the system 208 is a charge indication system for the electronic device 100. In some embodiments, the state of charge of the at least one battery 132 is a low state of charge.

In some embodiments, the at least one predefined time period is implemented in an off-on pattern such that the electronic device 100 is powered off for some time period and then powered on for a second time period. In some embodiments, a set of one or more interruptions do not substantially diminish intended function of the electronic device 100.

In some embodiments, the interruptions are configured to indicate a set of pre-defined states of charge. In some embodiments, the interruptions comprise approximately 1 milliseconds (ms), 10 ms, 100 ms, or 1 seconds (s) time periods that are separated from each other by time periods of approximately 1 ms, 10 ms, 100 ms, 1 s, or 10 s. In some embodiments, the interruptions comprise approximately 1 ms, 10 ms, 100 ms, time periods that are separated from each other by time periods of approximately 1 ms, 10 ms, 100 ms, or 1 s. In some embodiments, the interruptions comprise approximately 1 ms or 10 ms time periods that are separated from each other by time periods of approximately 1 ms, 10 ms, or 100 ms.

System 208 is configured to indicate a charge level in device 100 or, more specifically, a state of charge of battery 132. System 208 includes at least one battery 132. In some embodiments, system 208 includes a single battery 132. In some embodiments, system 208 may include multiple batteries 132. In such a situation, each of the multiple batteries 132 may be electrically connected to one another in a series configuration, a parallel configuration, or combinations thereof. Also, at least one battery 132 may include one or more electrochemical cells, such as alkaline cells, lithium-based cells, and so on, based on application requirements.

System 208 also includes at least one component 210. In some embodiments, component 210 is a motor 206 for fan 202 or blower 114 of respirator 102. Also, in some embodiments, system 208 includes a single component 210. In some embodiments, system 208 may include multiple components, such as multiple motors, and so on, based on application requirements. Component 210 is electrically connected to at least one battery 132 and configured to be powered by at least one battery 132. In some embodiments, when device 100 may be the headset, component 210 may be the driver of the headset. System 208 also includes a switch 212. Switch 212 is electrically connected to at least one battery 132 and component 210. Accordingly, switch 212 is configured to control power supply from at least one battery 132 to component 210, based on an operating position of switch 212. Switch 212 may be any electronic/electrical switch adapted to control power supply from a power source to a power consuming component, based on the operating position thereof.

System 208 further includes a controller 214. Controller 214 may be any control unit configured to perform various functions of the system 208. In some embodiments, controller 214 may be a dedicated control unit configured to perform functions related to system 208. In some embodiments, controller 214 may be a control unit associated with device 100 and configured to perform functions related to system 208. It should be noted that controller 214 may include a microprocessor device, such as a single chip microcontroller for computing information; a memory device, such as a flash Random Access Memory (RAM) for storing information, one or more input receivers for receiving signals from at least one battery 132 and component 210; and an output controller such as a modulation controller chip for providing signals to at least one battery 132 and component 210.

Also, the memory device may include a fixed memory populated with data, algorithms, calibration information, and/or programs for enabling the microprocessor to carry out calculations and procedures. Further, the memory device may include a temporary memory for storing data and information such as an operating parameter data collected during start-up and running of system 208. Accordingly, controller 214 may be disposed within device 100, such as within housing 120 of respirator 102. Controller 214 is communicably coupled to at least one battery 132, component 210, and switch 212. Accordingly, controller 214 is configured to determine the state of charge of at least one battery 132. The state of charge of battery at least one 132 may refer to a remaining charge level of at least one battery 132. The state of charge of at least one battery 132 may be generally expressed as a percentage of a reference value, such as 100 percent (%) of full capacity, 50% of full capacity, and so on. The state of charge of at least one battery 132 may be determined using any known method or technique of determining the state of charge, such as using voltage measurements, current measurements, pressure measurements, temperature measurements, chemical composition measurements, and so on, and/or a combination thereof.

Based on the determined state of charge of at least one battery 132, controller 214 is also configured to interrupt a function of component 210 for a predefined time period. As such, interrupting the function of component 210 is indicative of a low state of charge of at least one battery 132. In some embodiments, component 210 is motor 206 for fan 202 or blower 114 of respirator 102, and the function is driving of fan 202 or blower 114 by motor 206. In some embodiments, when device 100 may be the headset, component 210 may be the driver of the headset, and the function may be the active noise cancellation function of the headset. More specifically, interrupting the function of component 210 includes stopping power supply from at least one battery 132 to component 210 for a predefined time period. Accordingly, controller 214 is configured to actuate switch 212 to stop power supply from at least one battery 132 to component 210 for the predefined time period in order to interrupt the function of component 210. As such, controller 214 may actuate switch 212 in an open position to disconnect at least one battery 132 from component 210, thereby stopping power supply from at least one battery 132 to component 210 for a predefined time period.

Figure 3:
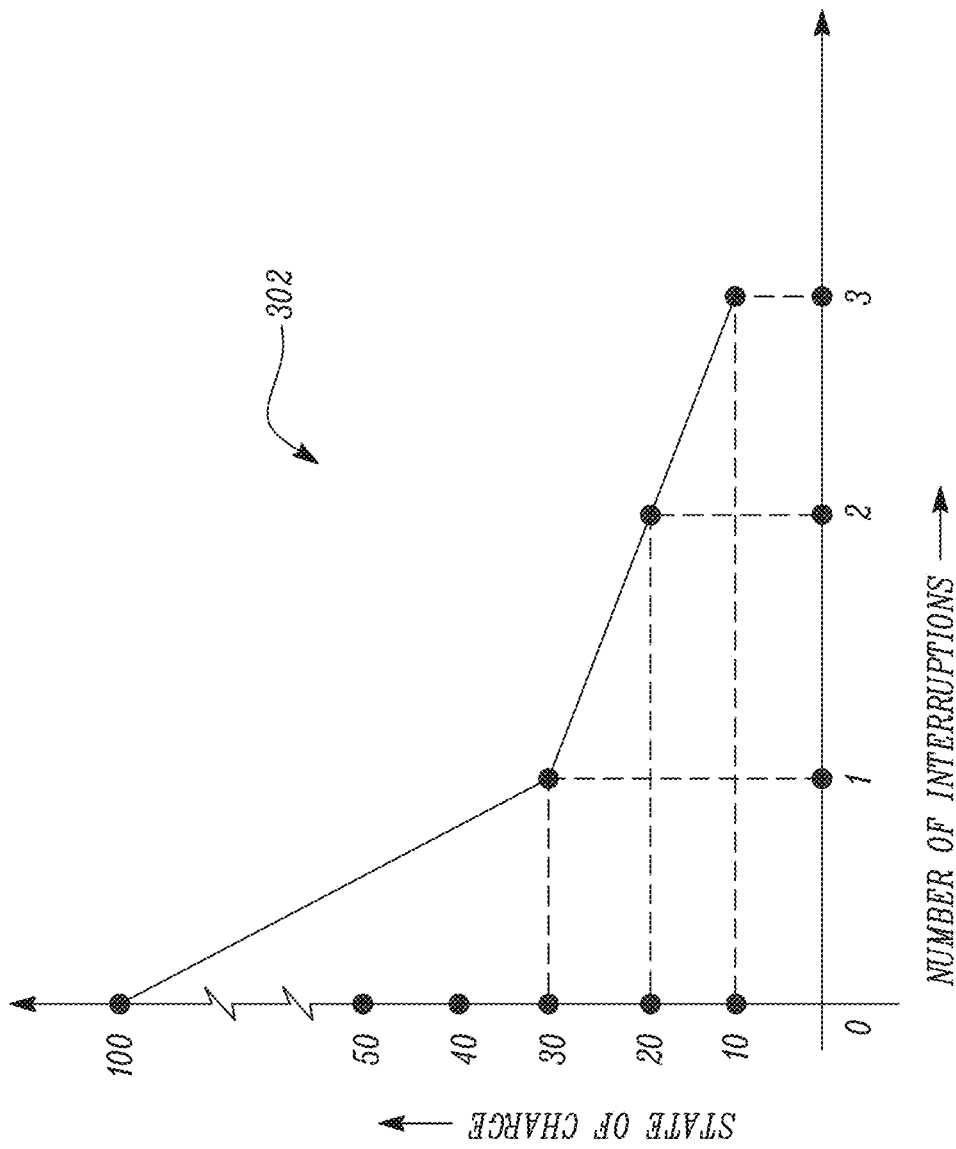
FIG. 3 is a graphical representation of working of the charge indication system of FIG. 2.

In some embodiments, the function of component 210 is interrupted for at least one first predefined time period based on a first state of charge of at least one battery 132. In some embodiments, the at least one first predefined time period may be a single predefined time period, such as 10 milliseconds (ms), 100 ms, 500 ms, 1000 ms, and so on. For example, referring to FIG. 3, a graphical representation 302 of a number of interruptions of the function of component 210 against the state of charge of at least one battery 132 is illustrated. As shown in the accompanying figure, as an exemplary embodiment, at approximately 30% state of charge of at least one battery 132 or approximately one hour of remaining state of charge of at least one battery 132, controller 214 may interrupt the function of component 210 for the single predefined time period, e.g., 100 ms, and may resume the function of component 210 after the single predefined time period is have elapsed. The 30% state of charge of at least one battery 132 or one hour of remaining state of charge of at least one battery 132 may be referred to as the first state of charge of at least one battery 132.

More specifically, in some embodiments, when the state of charge of at least one battery 132 is approximately 30%, controller 214 may interrupt the driving of fan 202 or blower 114 by motor 206 of respirator 102 for the at least one first predefined time period, e.g., 100 ms. After the at least one first predefined time period has elapsed, controller 214 may resume the driving of fan 202 or blower 114 by motor 206 of respirator 102. More specifically, controller 214 may actuate switch 212 in a closed position in order to connect at least one battery 132 to motor 206, thereby resuming power supply from at least one battery 132 to motor 206 in order to resume the driving of fan 202 or blower 114. A brief interruption of the function of component 210 for the at least one first predefined time period may provide an indication to user 108 of respirator 102 of the low state of charge of at least one battery 132, 30% in this case, without substantially disrupting a normal operation of respirator 102. In some embodiments, when device 100 may be the headset, and when the state of charge of at least one battery 132 is approximately 30%, controller 214 may interrupt the driver of the headset in order to interrupt the active noise cancellation function of the headset for the at least one first predefined time period, e.g., 100 ms. After the at least one first predefined time period has elapsed, controller 214 may resume the active noise cancellation function by the driver of the headset. The brief interruption of the function of component 210 for the at least one first predefined time period may provide an indication to user 108 of the headset of the low state of charge of battery 132, 30% in this case, without substantially disrupting a normal operation of the headset.

In some embodiments, the at least one first predefined time period may include a plurality of first predefined time periods. Also, the plurality of first predefined time periods may be spaced apart from each other by a third predefined time period. For example, in one embodiment, the plurality of first predefined time periods may include two predefined time periods, such that each of the two predefined time periods may be of 50 ms. Further, the two predefined time periods may be spaced apart by the third predefined time period, e.g., 100 ms.

As such, in an exemplary embodiment, when the state of charge of at least one battery 132 is approximately 30%, controller 214 may interrupt the function of respirator 102 twice for 50 ms each with the third predefined time period of 100 ms between each of the two interruptions. For example, when the state of charge of at least one battery 132 is approximately 30%, controller 214 may interrupt the function of respirator 102 for 50 ms. After the predefined time period of 50 ms has elapsed, controller 214 may resume the function of respirator 102 for the third predefined time period of 100 ms. After the third predefined time period of 100 ms has elapsed, controller 214 may again interrupt the function of respirator 102 for another 50 ms. After the predefined time period of 50 ms has elapsed, controller 214 may again resume the function of respirator 102. Such brief sequential interruptions of the function of component 210 may provide the indication to user 108 of respirator 102 of the low state of charge of at least one battery 132, 30% in this case, without substantially disrupting the normal operation of respirator 102. It should be noted that, in a situation when device 100 may be the headset, controller 214 may provide a similar pattern of interruptions of the driver of the headset for interrupting the active noise cancellation function of the headset. As such, controller 214 may provide the indication to user 108 of the headset of the low state of charge of at least one battery 132, 30% in this case, without substantially disrupting the normal operation of the headset.

In some embodiments, the function of component 210 is also interrupted for a plurality of second predefined time periods based on a second state of charge of at least one battery 132. The second state of charge is lower than the first state of charge. For example, referring to FIG. 3, as an exemplary embodiment, the second state of charge of at least one battery 132 is approximately 20% or half an hour of remaining state of charge of at least one battery 132. Also, the plurality of second predefined time periods may be spaced apart from each other by a fourth predefined time period. For example, in one embodiment, the plurality of second predefined time periods may include two predefined time periods, such that each of the two predefined time periods may be of 100 ms. Further, the two predefined time periods may be spaced apart by the fourth predefined time period, e.g., 200 ms.

As such, in an exemplary embodiment, when the state of charge of at least one battery 132 is approximately 20%, controller 214 may interrupt the function of respirator 102 twice for 100 ms each with the fourth predefined time period of 200 ms between each of the two interruptions. For example, when the state of charge of at least one battery 132 is approximately 20%, controller 214 may interrupt the function of respirator 102 for 100 ms. After the predefined time period of 100 ms has elapsed, controller 214 may resume the function of respirator 102 for the fourth predefined time period of 200 ms. After the fourth predefined time period of 200 ms has elapsed, controller 214 may again interrupt the function of respirator 102 for another 100 ms. After the predefined time period of 100 ms has elapsed, controller 214 may again resume the function of respirator 102. Such brief sequential interruptions of the function of component 210 may provide the indication to user 108 of respirator 102 of the low state of charge of at least one battery 132, 20% in this case, without substantially disrupting the normal operation of respirator 102. It should be noted that in a situation when device 100 may be the headset, controller 214 may provide a similar pattern of interruptions of the driver of the headset for the active noise cancellation function of the headset. As such, controller 214 may provide the indication to user 108 of the headset of the low state of charge of at least one battery 132, 20% in this case, without substantially disrupting the normal operation of the headset.

In the illustrated example, each of the plurality of second predefined time periods is approximately equal to the at least one first predefined time period. More specifically, in the illustrated example, each of the plurality of second predefined time periods is 100 ms. Also, the at least one first predefined time period is 100 ms, such that each of the plurality of second predefined time periods is approximately equal to the at least one first predefined time period. Additionally, in the illustrated example, each of the plurality of second predefined time periods is equal to one another, i.e., 100 ms. In other embodiments, one or more of the plurality of second predefined time periods may be different from one another and may have any other time value, such as 50 ms and 100 ms, 100 ms and 200 ms, 150 ms and 250 ms, and so on. Further, in the illustrated example, the plurality of second predefined time periods includes two predefined time periods. In other embodiments, the plurality of second predefined time periods may include any number of predefined time periods, such as three, four, and so on, based on application requirements. In such a situation, one or more of the plurality of second predefined time periods may have same or different time values, based on application requirements.

In some embodiments, each of the plurality of second predefined time periods may be greater than the at least one first predefined time period. For example, in such a situation, when the at least one first predefined time period may be 100 ms, each of the plurality of second predefined time periods may be greater than 100 ms, e.g., 200 ms, 500 ms, and so on. Also, one or more of the plurality of second predefined time periods may be different from one another and may have any other time value. In some embodiments, each of the plurality of second predefined time periods may be less than the at least one first predefined time period. For example, in such a situation, when the at least one first predefined time period may be 500 ms, each of the plurality of second predefined time periods may be less than 500 ms, e.g., 100 ms, 200 ms, and so on. Also, one or more of the plurality of second predefined time periods may be different from one another and may have any other time value.

In some embodiments, the function of the component 210 is also interrupted for a plurality of fifth predefined time periods based on a third state of charge of the at least one battery 132. The third state of charge is lower than the second state of charge. For example, referring to FIG. 3, in some embodiments, the third state of charge of at least one battery 132 is approximately 10% or fifteen minutes of remaining state of charge of at least one battery 132. Also, the plurality of fifth predefined time periods may be spaced apart from each other by a sixth predefined time period. For example, in some embodiments, the plurality of fifth predefined time periods may include three predefined time periods, such that each of the three predefined time periods may be of 100 ms. Further, the three predefined time periods may be spaced apart by the sixth predefined time period, e.g., 200 ms.

As such, in some embodiments, when the state of charge of at least one battery 132 is approximately 10%, the controller 214 may interrupt the function of respirator 102 thrice for 100 ms each with the sixth predefined time period of 200 ms between each of the three interruptions. For example, when the state of charge of at least one battery 132 is approximately 10%, controller 214 may interrupt the function of the respirator 102 for 100 ms. After the predefined time period of 100 ms has elapsed, controller 214 may resume the function of the respirator 102 for the sixth predefined time period of 200 ms. After the sixth predefined time period of 200 ms has elapsed, controller 214 may again interrupt the function of respirator 102 for another 100 ms. After the predefined time period of 100 ms has elapsed, controller 214 may again resume the function of respirator 102 for the sixth predefined time period of 200 ms. After the sixth predefined time period of 200 ms has elapsed, controller 214 may again interrupt the function of respirator 102 for another 100 ms. After the predefined time period of 100 ms has elapsed, controller 214 may again resume the function of the respirator 102. Such brief sequential interruptions of the function of component 210 may provide the indication to user 108 of respirator 102 of the low state of charge of at least one battery 132, 10% in this case, without substantially disrupting the normal operation of respirator 102. It should be noted that, in a situation when device 100 may be the headset, controller 214 may provide a similar pattern of interruptions of the driver of the headset for interrupting the active noise cancellation function of the headset. As such, controller 214 may provide the indication to user 108 of the headset of the low state of charge of a at least one battery 132, 10% in this case, without substantially disrupting the normal operation of the headset.

It should be noted that the different states of charge of at least one battery 132 described herein at which controller 214 may interrupt the function of device 100 are merely exemplary and may vary, based on application requirements. For example, controller 214 may be configured to interrupt the function of device 100 at any state of charge of at least one battery 132 other than 30%, 20%, and 10%, or one hour, half hour, and fifteen minutes of remaining state of charge of at least one battery 132 as described herein. It should also be noted that the at least one first predefined time period, the plurality of first predefined time periods, the plurality of second predefined time periods, the third predefined time period, the fourth predefined time period, the plurality of fifth predefined time periods, the sixth predefined time period, and so on, as described herein, are merely exemplary and may vary, based on application requirements. For example, controller 214 may be configured to interrupt the function of device 100 in any sequence or pattern in order to provide the indication to user 108 of the low state of charge of at least one battery 132 without substantially disrupting the normal operation of device 100.

It should further be noted that the time values of each of the at least one first predefined time period, the plurality of first predefined time periods, the plurality of second predefined time periods, the third predefined time period, the fourth predefined time period, the plurality of fifth predefined time periods, the sixth predefined time period, and so on, as described herein, are merely exemplary and may vary, based on application requirements. For example, controller 214 may be configured to interrupt the function of device 100 in any sequence or pattern using any suitable time values of interruption in order to provide the indication to user 108 of the low state of charge of at least one battery 132 without substantially disrupting the normal operation of device 100.

Figure 4:
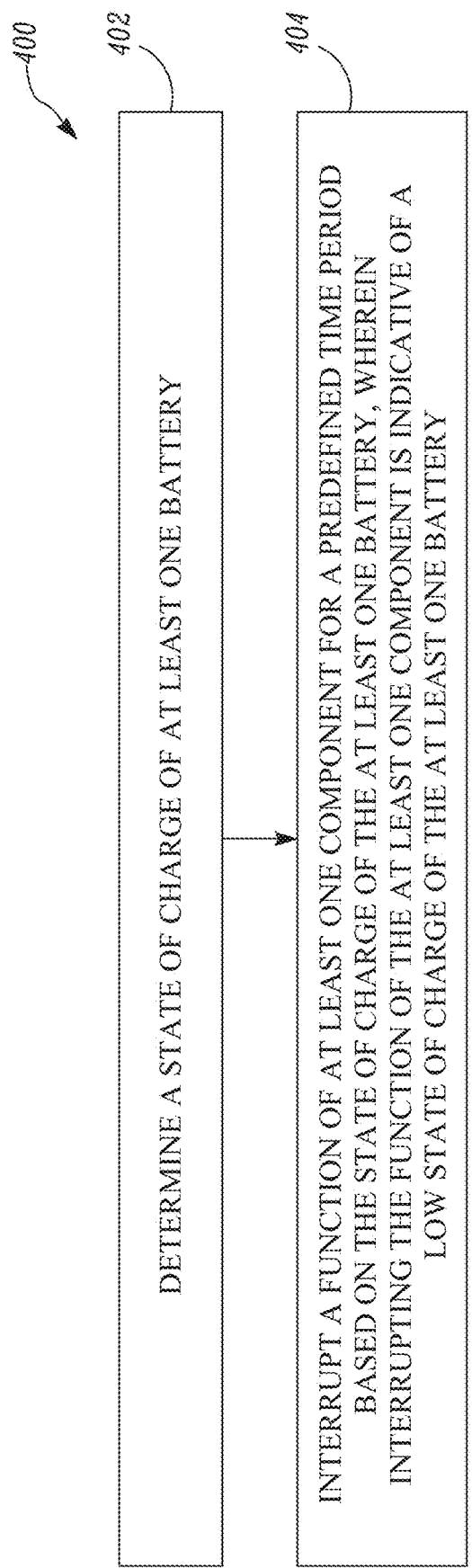
FIG. 4 is a flowchart of a method of working of the charge indication system of FIG. 2.

The present disclosure also relates to a method of indicating the charge level of device 100, and more specifically, to a method of operation of system 208. Referring to FIG. 4, a flowchart of a method 400 of indicating the charge level in device 100 is illustrated. At step 402, controller 214 determines the state of charge of at least one battery 132. At step 404, controller 214 interrupts the function of component 210 for the predefined time period based on the state of charge of at least one battery 132. More specifically, interrupting the function of component 210 is indicative of the low state of charge of at least one battery 132. In the illustrated embodiment, device 100 is respirator 102. Accordingly, component 210 is motor 206 of fan 202 or blower 114 of respirator 102, and the function is the driving of fan 202 or blower 114 by motor 206 of respirator 102. In another embodiment, device 100 may be the headset. Accordingly, component 210 may be the driver of the headset, and the function may be the active noise cancellation function of the headset.

Controller 214 interrupts the function of component 210 by stopping power supply from at least one battery 132 to component 210 for the predefined time period. More specifically, controller 214 actuates switch 212 to stop power supply from battery 132 to component 210 for the predefined time period. Based on the first state of charge of battery 132, controller 214 interrupts the function of component 210 for the at least one first predefined time period. In some embodiments, the at least one first predefined time period includes the plurality of first predefined time periods. In such a situation, the plurality of first predefined time periods are spaced apart from each other by the third predefined time period.

Further, based on the second state of charge of battery 132, controller 214 interrupts the function of component 210 for the plurality of second predefined time periods. The second state of charge is lower than the first state of charge. Also, the plurality of second predefined time periods are spaced apart from each other by the fourth predefined time period. In some embodiments, each of the plurality of second predefined time periods is approximately equal to the at least one first predefined time period. In some embodiments, each of the plurality of second predefined time periods may be greater than the at least one first predefined time period. In some embodiments, each of the plurality of second predefined time periods may be less than the at least one first predefined time period. Additionally, based on the third state of charge of at least one battery 132, at least one controller 214 interrupts the function of at least one component 210 for the plurality of fifth predefined time periods. The third state of charge is lower than the second state of charge. Also, the plurality of fifth predefined time periods are spaced apart from each other by the sixth predefined time period.

System 208 provides a simple, efficient, and effective method of indicating the state of charge of at least one battery 132 of device 100 to user 108 without substantially disrupting normal operation of device 100. In some embodiments, the interruptions of component 210 of device 100 may be substantially brief, such that the normal operation of respirator 102 may not be disrupted and yet user 108 may feel the interruption as component 210, since motor 206 in case of respirator 102 and the driver in case of the headset, may be attached to user 108. An actual time period of the interruptions may be configured in a manner to provide a relatively weak or a relatively strong buzz like feel to user 108 indicating the state of charge of at least one battery 132 of device 100. As such, user 108 would naturally relate the interruptions of the function of component 210 with low state of charge of at least one battery 132, in turn, improving usability and functionality.

Accordingly, system 208 may provide indication of the low state of charge to user 108 in situations when user 108 may be unable to access conventional indicators, such as lights, alarms, and so on. Additionally, in some embodiments, system 208 does not include the conventional indicators, such as lights, alarms, and so on, in turn, reducing excessive use of at least one battery 132 and improving usable runtime of at least one battery 132 during the low state of charge of at least one battery 132. System 208 may be incorporated in any electronic device with little or no modification to the existing system, in turn, improving compatibility. Further, system 208 includes simple components already existing on device 100, such as at least one battery 132, component 210, switch 212, controller 214, and so on, in turn, reducing bulk, complexity, and costs.

Unless otherwise indicated, all numbers expressing feature sizes, amounts, and physical properties used in the specification and claims are to be understood as being modified by the term "about". Accordingly, unless indicated to the contrary, the numerical parameters set forth in the foregoing specification and attached claims are approximations that can vary depending upon the desired properties sought to be obtained by those skilled in the art utilizing the teachings disclosed herein.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

The invention claimed is:

1. A system comprising:
   an electronic device powered by at least one battery,
   a controller communicably coupled to the at least one battery, wherein the controller is configured to:
   (a) determine a state of charge of the at least one battery; and
   (b) interrupt a function of the electronic device for at least one predefined time period based on the state of charge of the at least one battery,
   wherein interruption in (b) is indicative of a state of charge of the at least one battery, and
   wherein interrupting the function of the electronic device for the at least one predefined time period includes:
   interrupting the function of the electronic device for at least one first predefined time period based on a first state of charge of the at least one battery;
   interrupting the function of the electronic device for a plurality of second predefined time periods based on a second state of charge of the at least one battery, wherein the second state of charge is lower than the first state of charge; and
   stopping power supply from the at least one battery to at least one component of the electronic device for the predefined time period;
   wherein:
   the electronic device is a respirator,
   the at least one component is a motor of the respirator, and
   the function is driving of a fan of the respirator by the motor.

2. The system of claim 1, wherein the system is a charge indication system for the electronic device.

3. The system of claim 1, wherein the state of charge of the at least one battery is a low state of charge.

4. The system of claim 1, wherein the at least one predefined time period is implemented in an off-on pattern such that the electronic device is powered off for some time period and then powered on for a second time period.

5. The system of claim 1, wherein a set of one or more interruptions in (b) do not substantially diminish intended function of the electronic device.

6. The system of claim 1, wherein the interruptions in (b) are configured to indicate a set of pre-defined states of charge.

7. The system of claim 1, wherein the interruptions comprise approximately 1 ms, 10 ms, 100 ms, or 1 s time periods that are separated from each other by time periods of approximately 1 ms, 10 ms, 100 ms, 1 s, or 10 s.

8. The system of claim 1, wherein the interruptions comprise approximately 1 ms, 10 ms, or 100 ms time periods that are separated from each other by time periods of approximately 1 ms, 10 ms, 100 ms, or 1 s.

9. The system of claim 1, wherein the interruptions comprise approximately 1 ms or 10 ms time periods that are separated from each other by time periods of approximately 1 ms, 10 ms, or 100 ms.

10. The charge indication system of claim 1, wherein each of the plurality of second predefined time periods is approximately equal to the at least one first predefined time period.

11. The charge indication system of claim 1, wherein each of the plurality of second predefined time periods is greater than the at least one first predefined time period.

12. The charge indication system of claim 1, wherein each of the plurality of second predefined time periods is less than the at least one first predefined time period.

13. The charge indication system of claim 1, wherein the at least one first predefined time period includes a plurality of first predefined time periods, the plurality of first predefined time periods being spaced apart from each other by a third predefined time period.

14. The charge indication system of claim 1, wherein the plurality of second predefined time periods are spaced apart from each other by a fourth predefined time period.

15. The charge indication system of claim 1 further comprising a switch communicably coupled to the controller and adapted to control power supplied from the at least one battery to at least one component of the electronic device, and wherein interrupting the function of the electronic device further includes actuating the switch to stop power supplied from the at least one battery to the at least one component of the electronic device for the at least one predefined time period.

\* \* \* \* \*